United States Patent [19]

Bellos

[11] 4,368,137
[45] Jan. 11, 1983

[54] POLYMERS OF OXYALKYLATED PIPERAZINES AND USES THEREOF

[75] Inventor: Thomas J. Bellos, Kirkwood, Mo.

[73] Assignee: Petrolite Corporation, St. Louis, Mo.

[21] Appl. No.: 264,722

[22] Filed: May 18, 1981

[51] Int. Cl.³ .............................................. C08G 65/34
[52] U.S. Cl. .................................... 252/344; 525/417; 528/423; 544/357
[58] Field of Search ....................... 252/344; 528/423; 544/357; 525/417

[56] References Cited

U.S. PATENT DOCUMENTS

| | | | |
|---|---|---|---|
| 3,009,884 | 11/1961 | Monson et al. | 252/341 |
| 3,532,646 | 10/1970 | Antikow et al. | 528/423 |
| 4,013,787 | 3/1977 | Varlerberghe et al. | 528/423 |

Primary Examiner—Maurice J. Welsh
Attorney, Agent, or Firm—Sidney B. Ring; Hyman F. Glass

[57] ABSTRACT

This invention relates to polymerized oxyalkylated piperazines, to the salts and quaternaries thereof; and to uses thereof for example as demulsifiers, flotation aids, etc.

16 Claims, No Drawings

POLYMERS OF OXYALKYLATED PIPERAZINES AND USES THEREOF

In U.S. Pat. No. 3,009,884 there are described polymers prepared by polymerizing acylated alkanolamines such as fatty acid acylated triethanol amines to yield polymers containing polyether linkages.

I have now discovered that polymers of oxyalkylated piperazines can be prepared to yield products having a wide variety of uses such as flocculants, flotation agents, etc.

The polymers are prepared by heating oxyalkylated piperazines under polymerizing conditions such as under heat, with or without catalysts, such as $ZnCl_2$, $ZnCl_2$/Acetic Acid, Phosphoric acid, Iron, $Al_2(SO_4)_3$ or combinations of metals and/or salts and acids, e.g., Fe/Acetic, Fe/$ZnCl_2$. The temperature for polymerization is from about 220° to 300° C., such as from about 240° to 260°, but preferably from about 260° to 275°.

The polymerization reaction can be ideally presented as follows:

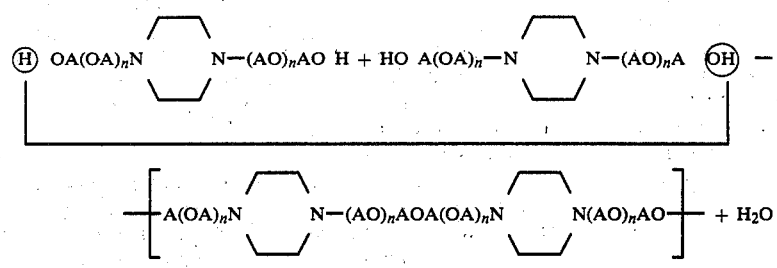

Piperazine, the amine which is oxyalkylated, has the formula:

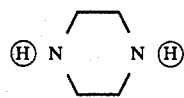

It may be oxyalkylated at the encircled (H) to yield a difunctional oxyalkylate:

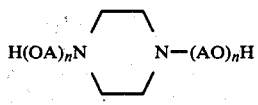

where OA is the oxyalkyl group such as ethylene, propylene, butylene, higher alkylenes, etc., mixtures thereof, blocks thereof, etc.

Substituted piperazines may also be employed for example of the formula:

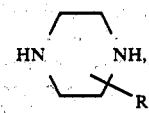

where R is a hydrogen or a substituted group which does not interfere with oxyalkylation, for example, alkyl, cycloalkyl, aryl, etc., and n is an integer:

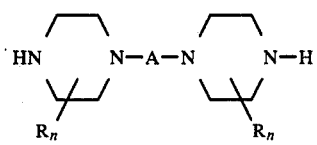

where A is a bridging group such as alkylene $-CH_2-_n$, alkyleneether $-CH_2)_2-O-CH_2-$, arylene such as

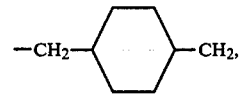

The agents employed in oxyalkylating piperazines are alkylene oxides such as ethylene oxide, propylene oxide, butylene, and higher oxides. They may be added individually, as mixtures, as "blocks" of one oxide then another oxide, etc.

The moles of oxide added per mole of piperazine can vary widely depending on the particular oxides or combination of oxides, the use intended, etc. In general, from about 1 to 6 or more moles of oxide are added per mole of piperazine, for example from about 3 to 4 moles, such as from about 1.8 to 2.5 moles, but preferably from about 1.0 to 2.0 moles.

The following examples are presented for purposes of illustration and not of limitation.

Piperazine is oxyalkylated in the conventional manner. For example piperazine is charged to a suitable pressure reactor, the reactor evacuated to remove air, heated to elevated temperatures such as 100°–135° C. with stirring and the desired amount of ethylene oxide added at 20–150 psi and reacted until zero psi is achieved indicating complete reaction of ethylene oxide.

To form the polymerized product the oxyalkylated product is heated in a reactor in the presence of a suitable catalyst at elevated temperatures such as from 225°–300° C. until the desired amount of water is removed which indicates the desired amount of polymerization.

The following are illustrative examples.

| Ex. | Oxyalkylates Moles of Oxide per Moles of piperazine moles EtO | PRO | Temperature of Oxyalkylation | Polymerization Weight Oxyalkylated piperazine | Temperature Polymerization °C. | Type & Weight Catalyst | Weight* of Condensate Removed |
|---|---|---|---|---|---|---|---|
| 1 | 2 | — | 80–100° C. | 300 g | 240–290 | ZnCl$_2$/3 g Acetic 3 g | 68.4 g |
| 2 | 2 | — | 80–100° C. | 300 g | 265–280 | Fe/7 g | 60.0 g |
| 3 | 2 | 1 | 115° C. | 300 g | 275 | H$_3$PO$_4$/6 g | 62 g |
| 4 | — | 2 | 115° C | 350 g | 280 | H$_3$PO$_4$/6 g | 78.5 g |
| 5 | — | 2 | 115° C. | 300 g | 290 | Fe/8 g | 64.2 g |
| 6 | — | 3 | 115° C. | 300 g | 290 | H$_3$PO$_4$/7 g | 69.0 g |
| 7 | 3 | — | 115° C. | 300 g | 275 | ZnCl$_2$ 3.5 g Acetic 3.5 g | 64.2 g |
| 8 | — | 3 | 115° C. | 300 g | 290 | ZnCl$_2$ 5 g Acetic 4 g | 71.0 g |
| 9 | 2 | 1 | 115° C. | 305 g | 275 | Fe/5.4 g | 61.2 g |
| 10 | 2 | — | 115° C. | 300 g | 275 | H$_3$PO$_4$/9 g | 59.8 g |
| 11 | 2 | 1 | 115° C. | 300 g | 280 | Fe/10 g | 61.8 g |
| 12 | 1 | 1 | 115° C. | 407 g | 270 | ZnCl$_2$ 2.67 g Acetic 2.54 g | 53 g |
| 13 | 1 | 1 | 115° C. | 304 | 275–285 | ZnCl$_2$ 3.33 g Acetic 3.46 g | 71.75 g |

*Condensate is a complex mixture of water of condensation, distillation products and products of decomposition generated by the pyrolysis of the monomer.

The composition of this invention are generally employed in salt or quaternary form. Any suitable salt or quaternary can be formed. In practice, it is convenient to employ the acid and quaternizing agent conventionally employed such as hydrohalide acid such as HCl, HBr, etc., organic acids such as acetic, proprionic, benzoic, etc., alkylating agents such as alkyl halides, aryl halide such as benzyl halides, etc., difunctional alkylene halides such as Cl(CH$_2$)$_n$Cl, etc., ether-containing dihalides such as ClCH$_2$CH$_2$OCH$_2$CH$_2$Cl, etc., unsaturated dihalides such as ClCH$_2$CH=CHCH$_2$Cl, etc.

Any suitable acid may be employed whether inorganic, organic, or combinations thereof.

The anion derived from the acid which may vary widely may be for example, halide (Cl, Br, I, F), chlorates, carboxylates, such as derived from aliphatic acids, acetates, proprionates, aromatic acids, for example, benzoates, salicilates, phthalates, etc., phosphate, sulfate, sulfonate, etc. The salt is employed at a pH on the acid side, i.e., below about pH 7, such as from about 6.9 to 1.0, for example from about 6.9 to 3.0, but preferably from about 2.0 to 6.8, with an optimum of about 3.0 to 6.5.

This phase of the invention relates to a process for resolving or separating emulsions of the oil-in-water class, by subjecting the emulsion to the action of the compositions of this invention.

Emulsions of the oil-in-water class comprise organic oily materials, which, although immiscible with water or aqueous or non-oily media, are distributed or dispersed as small drops throughout a continuous body of non-oily medium. The proportion of dispersed oily material is in many and possibly most cases a minor one.

Oil-field emulsions containing small proportions of crude petroleum oil relatively stably dispersed in water or brine are representative oil-in-water emulsions. Other oil-in-water emulsions include: steam cylinder emulsions, in which traces of lubricating oil are found dispersed in condensed steam from steam engines and steam pumps; oil-in-water emulsions occurring in the cooling water systems of gasoline absorption plants; emulsions of petroleum residues-in-diethylene glycol, in the dehydration of natural gas, etc.

In other industries and arts, emulsions of oily materials in water or other non-oily media are encountered, for example, in sewage disposal operations, milk and mayonnaise processing, marine ballast water disposal. In cleaning the equipment used in processing such products, diluted oil-in-water emulsions are inadvertently, incidentally, or accidentally produced. The disposal of aqueous wastes is, in general, hampered by the presence of oil-in-water emulsions.

Steam distillation and other production procedures sometimes cause oil-in-water emulsions to be produced, from which the valuable oils are difficultly recoverable.

In all such examples, a non-aqueous or oily material is emulsified in an aqueous or non-oily material with which it is naturally immiscible. The term "oil" is used herein to cover broadly the water-immiscible materials present as dispersed particles in such systems. The non-oily phase obviously includes diethylene glycol, aqueous solutions, and other non-oily media in addition to water itself.

Among the most important emulsions of non-saponifiable material in water are petroleum oil-in-water emulsions.

Oil-in-water emulsions contain widely different proportions of dispersed phase. Where the emulsion is a waste product resulting from the flushing with water of manufacturing areas or equipment, the oil content may be only a few parts per million. Naturally-occurring oil-field emulsions of the oil-in-water class carry crude oil in proportions varying from a few parts per million to about 20%, or even higher in rare cases.

The present invention is concerned with the resolution of those emulsions of the oil-in-water class which contain a minor proportion of dispersed phase, ranging from 20% down to a few parts per million.

Although the present invention relates to emulsions containing as much as 20% dispersed oily material, many if not most of them contain appreciably less than this proportion of dispersed phase. In fact, most of the emulsions encountered in the development of this invention have contained about 1% or less of dispersed phase. It is to such oil-in-water emulsions having dispersed phase volumes of the order of 1% or less to which the present process is particularly directed. This does not mean that any sharp line of demarcation exists, and that, for example, an emulsion containing 1.0% of dispersed phase will respond to the process, whereas one containing 1.1% of the same dispersed phase will remain unaffected; but that, in general, dispersed phase proportions of the order of 1% or less appear most favorable for application of the present process.

The present process, as stated above, appears to be effective in resolving emulsions containing up to about 20% of dispersed phase. It is particularly effective on emulsions containing not more than 1% of dispersed phase, which emulsions are the most important, in view of their common occurrences.

Some emulsions are by-products of manufacturing procedures in which the composition of the emulsion and its ingredients is known. In many instances, however, the emulsions to be resolved are either naturally-occurring or are accidentally or unintentionally produced; or in any event they do not result from a deliberate or premeditated emulsification procedure. In numerous instances, the emulsifying agent is unknown; and as a matter of fact an emulsifying agent, in the conventional sense, may be felt to be absent. It is obviously very difficult or even impossible to recommend a resolution procedure for the treatment of such latter emulsions, on the basis of theoretical knowledge. Many of the most important applications of the present process are concerned with the resolution of emulsions which are either naturally-occurring or are accidentally, unintentionally, or unavoidably produced. Such emulsions are commonly of the most dilute type, containing about 1% or less of dispersed phase, although concentrations up to 20% are herein included, as stated above.

The process which constitutes the present invention consists in subjecting an emulsion of the oil-in-water class to the action of the compositions of this invention, thereby causing the oil particles in the emulsion to coalesce sufficiently to rise to the surface of the non-oily layer (or settle to the bottom, if the oil density is greater), when the mixture is allowed to stand in the quiescent state after treatment with the compositions of this invention.

Applicability of the present process can be readily determined by direct trial on any emulsion, without reference to theoretical considerations. This fact facilitates its application to naturally-occurring emulsions, and to emulsions accidentally, unintentionally, or unavoidably produced; since no laboratory experimentation, to discover the nature of the emulsion components or of the emulsifying agent, is required.

The compositions of this invention herein described for resolution of oil-in-water type emulsions may be used alone or in combination with other products which also are effective for resolution of oil-in-water emulsions, for example, in combination with electrolytes.

Examples of electrolytes which were found to be suitable are: $FeCl_3$, $ZnCl_2$, $Al_2(SO_4)_3$, $AlCl_3$, etc.

The present reagents are useful, because they are able to recover the oil from oil-in-water-class emulsions more advantageously and at lower cost than is possible using other reagents or other processes. In some instances, they have been found to resolve emulsions which were not economically or effectively resolvable by any other known means.

The compositions of this invention may be employed alone, or they may in some instances be employed to advantage admixed with other and compatible oil-in-water demulsifiers.

The process is commonly practised simply by introducing small proportions of the compositions of this invention into an oil-in-water-class emulsion, agitating to secure distribution of the reagent and incipient coalescence, and letting stand until the oil phase separates. The proportion of the compositions required will vary with the character of the emulsion to be resolved. Ordinarily, proportions of the composition required are from 1/5,000 to 1/500,000 the volume of emulsion treated; but more is sometimes required.

In some instances, importantly improved results are obtained by adjusting the pH of the emulsion to be treated, to an experimentally determined optimum value.

The composition feed rate also has an optimum range, which is sufficiently wide, however, to meet the tolerances required for the variances encountered daily in commercial operations. A large excess of the compositions of this invention can produce distinctly unfavorable results.

The manner of practicing the present invention is clear from the foregoing description.

The compositions of this invention are useful in the clarification of water containing emulsified oil or suspended oily solids. The application is especially effective for the resolution of oil-in-water emulsions as encountered in oil fields, oil-in-water emulsions resulting from refinery processes and emulsions of cutting and rolling oils from metal working industries. The compositions of this invention may be used in simple settling tanks or basins.

The compositions of this invention are employed as reagents in removing oils, solids, and combinations thereof from aqueous systems. They are particularly effective as such a reagent in flotation systems.

REMOVAL OF OILS AND SOLIDS FROM AQUEOUS SYSTEMS

In the present process, to remove oils, or solids, or combinations thereof, from aqueous systems, the reagent is introduced at any convenient point in the system, and it is mixed with the oils or solids in any desired manner, such as by being pumped or circulated through the system or by mechanical agitation such as paddles or by gas agitation. After mixing, the mixture of oils or solids and reagent is allowed to stand quiescent until the constituent phases of the emulsion separate. Settling times and optimum mixing times will, of course, vary with the nature of the oil or solid and the apparatus available. The operation, in its broadest concept, is simply the introduction of the reagent into the oils or solids, the mixing of the two to establish contact and promote coalescence, and, usually, the subsequent quiescent settling of the agitated mixture, to produce the aqueous and non-aqueous phases as stratified layers.

Agitation may be achieved in various ways. The piping system through which the oil- or solids-containing system is passed during processing may itself supply sufficient turbulence to achieve adequate mixing of reagent and system. Baffled pipe may be inserted in the flow sheet to provide agitation. Other devices such as perforated-chamber mixers, excelsior- or mineral- or gravel- or steel-shaving-packed tanks, beds of stones or gravel or minerals in open ducts or trenches may be employed beneficially to provide mixing. The introduction of a gas, such as natural gas or air, into a tank or pipe in which or through which the mixture of reagent and system is standing or passing is frequently found suitable to provide desired agitation.

It has been found that the factors, reagent feed rate, agitation, and settling time are somewhat interrelated. For example, with sufficient agitation of proper intensity the settling time required can be materially shortened. On the other hand, if agitation is relatively non-procurable but extended settling time is, the process may be equally productive of satisfactory results. The reagent feed rate has an optimum range, which is sufficiently wide, however, to meet the tolerances required for the variances encountered daily in commercial operations.

Application of a suitable gas in a procedure approximating that of the froth flotation cell employed in ore beneficiation, after the present reagent has been added to the system to be resolved, frequently has a favorable influence of totally unexpected magnitude. By incorporating the step of subjecting the chemicalized (i.e., containing the reagent) system to the action of air in a sub-aeration type flotation cell, a clear aqueous layer is sometimes obtained in a matter of seconds, without added quiescent settling and with approximately as much reagent. Natural gas was found to be as good a gaseous medium as was air, in this operation.

It should be distinctly understood that such aeration technique, while an important adjunct to the use of the present reagent, in some cases, is not an equivalent procedure. This may be proved by subjecting an un-chemicalized system to aeration for a period of minutes without detectable favorable effect. Addition of the reagent to such aerated system will produce resolution, promptly.

The details of the mechanical structures required to produce aeration suitable for the present purpose need not be given here. It is sufficient to state that any means capable of producing small gas bubbles within the body of the system is acceptable for use.

The flotation principle has long been employed in the beneficiation of ores. Many patents in this art illustrate apparatus suitable for producing aeration of liquids. Reference is made to Taggart's "Handbook of Ore Dressing," which describes a large number of such devices.

Suitable aeration is sometimes obtainable by use of the principle of Elmore, U.S. Pat. No. 826,411. In that ore beneficiation process, an ore pulp was passed through a vacuum apparatus, the application of vacuum liberating very small gas bubbles from solution in the water of the pulp, to float the mineral. A more recent application of this same principle is found in the Door "Vacuator."

The manner of practicing the present invention using aeration is clear from the foregoing description.

The order in which the compositions of this invention and the aeration step are applied is relatively immaterial. Sometimes it is more convenient to chemicalize the system and subsequently to apply the aeration technique. In others, it may be more advantageous to produce a strongly frothing system and then introduce the compositions into such aerated system.

Any desired gas can be substituted for air. Other commonly suitable gases include natural gas, nitrogen, carbon dioxide, oxygen, etc., the gas being used essentially for its levitation effect. If any gas has some deleterious effect on any component of the system, it will obviously be desirable to use instead some other gas which is inert under the conditions of use.

The amount of compositions of this invention used will vary depending on the particular composition, the particular system, etc. In general, the amount of composition employed in the system is at least about 0.5 ppm, such as from about 1.0 to 60 ppm, for example from about 5 to 40 ppm, but preferably from about 3.0 to 30 ppm. Larger amounts may be used but there is generally no cost/performance reason for so doing.

WEMCO Depurator Flotation Machine is a flotation machine for removal of emulsified oily wastes and suspended solids from petroleum industry wastewater.

The WEMCO Depurator unit employs mechanically-induced air flotation to separate solids, oils, or organic materials from refinery or oil field effluent in larger volumes, in less space, and at lower cost than any other machine. It can clean large quantities of wastewater containing from 200 to 5,000 ppm of oil, depending on the type of oil and emulsion. In most applications, less than 10 ppm of oil remain after a four-minute cleaning cycle.

It is available in a variety of sizes to handle from 1,720 to 171,000 barrels of wastewater per day. Depurator machines can be installed at costs 15-40% less than other comparable flotation equipment. Maintenance costs are lower, too. The Depurator unit also requires at least 50% less space than comparable equipment for its volume capacity. Over 300 successful field installations to date.

WEMCO Depurator units are composed of four standard WEMCO flotation cells. Each cell is equipped with a motor-driven self-aerating rotor mechanism. As the rotor spins, it acts as a pump, forcing water through a disperser and creating a vacuum in the standpipe. The vacuum pulls gas into the standpipe and thoroughly mixes it with the wastewater. As the gas/water mixture travels through the disperser at high velocity, a shearing force is created, causing the gas to form minute bubbles. Oil particles and suspended solids attach to the gas bubbles as they rise to the surface. The oil and suspended solids gather in a dense froth on the surface, are removed from the cell by skimmer paddles and collected in external launders.

In the majority of applications, natural gas or nitrogen is used to form the bubbles. The absence of oxygen prevents the growth of harmful bacteria and also reduces downstream corrosion. A pressure of 0.50 to 1.0 ounce maintains a gas blanket between the liquid level and gas-tight cover. When air is used, it is induced by the Depurator machine at atmospheric pressure. Self-induced mechanical air flotation eliminates need for auxiliary air compressors or blowers.

Processing is often improved with the aid of a chemical injected into the water upstream from the float cell. These compounds break oil-in-water emulsions, gather suspended solids, and stabilize the air bubbles to promote froth flotation.

The Depurator machine consists of a self-supporting, all-steel skid-mounted tank, with integral float-collecting flumes and gas-tight covers. Tank interior is high-temperature epoxy coated for greatest corrosion resistance. Inspection doors are provided on both sides of the tank, plus a breather valve and pneumatic liquid level controller.

Each standpipe is equipped with gas intake ports beneath the gas-tight cover. A separate motor powers each rotor/disperser mechanism. Two $\frac{1}{4}$ horsepower gearmotors drive the skimmer assemblies. All motors are explosion-proof, 3 phase, 60 cycle, 230/460 volt.

The following are the major petroleum industry applications.

OIL FIELD PRODUCTION WATER

The Depurator machine wrings almost the final drops of oil from produced water. After initial treatment by gravity oil/water separators, such as free water knockouts, gun barrels, and skim tanks, oilfield water can be terminally cleaned to most community and company standards by the WEMCO Depurator machine. Depurator units will remove the emulsified oil left by preliminary water treatment which could prevent formation plugging and reduce pump efficiency when the water is to be reinjected for water flooding. For steam flooding, the Depurator unit is used ahead of boiler pretreatment equipment.

If the wastewater is to be disposed of by percolation ponds, or returned to existing waterways, the Depurator machine has consistently proven its ability to clean the water to local, state and federal standards.

REFINERY PROCESS WATER

At the refinery, the Depurator wastewater treatment generally follows gravity oil-water separation. The wastewater includes process water from desalters, tank and water drawoffs, steam stripping condensate, pump gland cooling, barometric condenser, treating plant wash, caustic treatment, and loading facility washdown. It may also include storm run-off water.

The Depurator device is first choice for secondary wastewater treatment because, unlike gravity oil-water separators, it will break emulsions with appropriate chemical additives. More than a dozen successful installations are currently in refinery operation.

PETROCHEMICAL WASTEWATER

Wastewater created in the production of bulk chemicals derived from natural gas or petroleum is often distinguished from the usual oil refinery product by special characteristics. No single oil/water separation method has proven capable of handling all the compounds produced. The flotation process, as employed by the WEMCO Depurator machine, has proven to be the best wastewater treatment for many of these oils and suspended solids. Bench tests are recommended for each specific application.

BALLAST WATER

Rarely is it possible to discharge water directly into the bay or waterway from ballast water storage tanks. Depurator units take the water from the storage tank and make the precise oil-water separation necessary to meet government clean water standards. Depurator flotation machines, with appropriate chemical additives, can break emulsions and reduce oily waste content of ballast water to lower levels than any other flotation process.

The following examples are presented for purposes of illustration and not of limitation.

Products of examples 1, 4, 8 and 12 were evaluated as reverse demulsifiers at a location in California. The products were evaluated as prepared and diluted with solvents and adjusted to a pH suitable to render the products soluble pH 1.0–4.5. Typically acetic acid, HCl, hydroxyacetic and etc., may be used to adjust the pH downward to an acceptable pH. These products were tested in the following fashion: 100 ml of test water (oilfield water containing produced oil and water) were placed in 150 ml test bottles—to each series of bottles an amount of chemical was added to each bottle to test each product, e.g., six bottles each contain 100 ml of water and e.g., 2, 4, 6, 8, 10 and 12 ppm of chemical agent. The bottles are next agitated via shaking by hand or machine for e.g., 100 shakes. The bottles are observed: Object of the testing is to determine which product or products cause the emulsion to break and exhibit the cleanest or most oil-free water (oil floats to the top of water if demulsifier is effective). The products may be tested against the prepared series, but usually they are tested against a field standard (FS). In addition, water can be decanted or syphoned from these test bottles and the oil content remaining is the water measured by extraction, wherein the treated water sample is decanted the residual oil extracted via a solvent, e.g., carbon tetrachloride, Freon-117-113 and the resulting solution measured via an IR Analyzer calibrated to read *all* $CH_2$ groups, yielding a ppm level of oil in the water.

At a location in California products were evaluated against a field standard (FS) with the following results.

TABLE I

| | | California Location | | | |
|---|---|---|---|---|---|
| PRODUCT | NO. SHAKES | CHEMICAL CONTENT (ppm) | WATER TEMP. | ppm OBSERVED OIL AFTER TREATMENT* | COMMENTS |
| Blank | 100 | none | 150–180° C. | 200 ppm+ | |
| FS | " | 6 | " | 150 | |
| FS | " | 10 | " | 112 | |
| FS | " | 12 | " | 78 | |
| Ex. 1 | " | 6 | " | 110 | |
| Ex. 1 | " | 10 | " | 98 | |
| Ex. 1 | " | 12 | " | 36 | fast break |
| Ex. 4 | " | 6 | " | 180 | |
| Ex. 4 | " | 10 | " | 105 | |
| Ex. 4 | " | 12 | " | 58 | slower than #1 |
| Ex. 8 | " | 6 | " | 138 | |
| Ex. 8 | " | 10 | " | 105 | |
| Ex. 8 | " | 12 | " | 64 | slower than 1 & 4 |
| Ex. 12 | " | 6 | " | 156 | slower than 1 & 4 |
| Ex. 12 | " | 10 | " | 108 | |
| Ex. 12 | " | 12 | " | 71 | |
| Ex. 1 | " | 6 | " | 108 | best of group |
| Ex. 1 | " | 10 | " | 79 | |

TABLE I-continued

| | | California Location | | | |
|---|---|---|---|---|---|
| PRODUCT | NO. SHAKES | CHEMICAL CONTENT (ppm) | WATER TEMP. | ppm OBSERVED OIL AFTER TREATMENT* | COMMENTS |
| Ex. 1 | " | 12 | " | 32 | |

*Water extracted filtered and oil in solutions (emulsion) measured by extraction in carbon tetrachloride are measured by Miran-Al (IR) Analyzer.

The above examples were further chemically modified by the preparation of quaternary ammonium salts of the polymers. Example 1—polymer was analyzed for its total nitrogen content as well as its primary, secondary and tertiary amine content. Essentially these products are tertiary in nature. Based on these analyses the products were converted to their quaternary salts via methylation with methyl chloride, ideally presented by the formula:

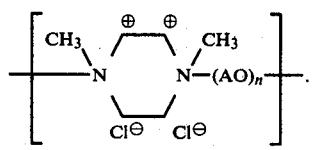

n = 1-6

These products were evaluated at the same location and while the order of best to poorest didn't change, product example 1 gave the following results when tested against its acid salt and the FS.

TABLE II

| PRODUCT | SHAKES | PPM CHEMICAL | WATER TEMP. | PPM OIL AFTER TREATMENT | COMMENTS |
|---|---|---|---|---|---|
| Blank | 100 | None | 190° | 2000+ | |
| FS | 100 | 6 | | 172 | |
| FS | 100 | 10 | | 150 | |
| FS | 100 | 12 | | 82 | |
| Ex. 1 | 100 | 6 (acid salt) | | 122 | |
| Ex. 1 | 100 | 10 (acid salt) | | 92 | |
| Ex. 1 | 100 | 12 (acid salt) | | 43 | |
| Mod. 1 | 100 | 6 (methyl quat) | | 112 | Best of group |
| Mod. 1 | 100 | 10 (methyl quat) | | 83 | Best of group |
| Mod. 1 | 100 | 12 (methyl quat) | | 27 | Best of group |

Therefore, it is observed that the chemical modification of these examples in some instances, up grades the results. In some instances these products may be formulated with additional organic and inorganic salts that enhance treating results, e.g., inorganics—Alum, $ZnCl_2$, $FeCl_2$, etc.

I claim:

1. A composition of matter comprising oxyalkylated piperazine polymerized by dehydration, or the salts or quaternaries thereof.

2. The composition of claim 1 where the oxyalkylated piperazine is oxyethylated.

3. The composition of claim 2 where the molar ratio of alkylene oxide to piperazine is about 1-6/1.

4. The composition of claim 3 where the molar ratio of ethylene oxide to piperazine is about 1-6/1.

5. The composition of claim 1 where about 1-3 moles of water are removed per mole of oxyalkylated piperazine.

6. The composition of claim 2 where about 1-3 moles of water are removed per mole of oxyalkylated piperazine.

7. The composition of claim 3 where about 1-3 moles of water are removed per mole of oxyalkylated piperazine.

8. The composition of claim 4 where about 1-3 moles of water are removed per mole of oxyalkylated piperazine.

9. A process of demulsification which comprises treating an emulsion with the composition of claim 1.

10. A process of demulsification which comprises treating an emulsion with the composition of claim 2.

11. A process of demulsification which comprises treating an emulsion with the composition of claim 3.

12. A process of demulsification which comprises treating an emulsion with the composition of claim 4.

13. A process of demulsification which comprises treating an emulsion with the composition of claim 5.

14. A process of demulsification which comprises treating an emulsion with the composition of claim 6.

15. A process of demulsification which comprises treating an emulsion with the composition of claim 7.

16. A process of demulsification which comprises treating an emulsion with the composition of claim 8.

* * * * *

UNITED STATES PATENT AND TRADEMARK OFFICE
CERTIFICATE OF CORRECTION

PATENT NO. : 4,368,137
DATED : January 11, 1983
INVENTOR(S) : Thomas J. Bellos

It is certified that error appears in the above—identified patent and that said Letters Patent is hereby corrected as shown below:

Col. 9 and 10: In Table I, under the water temp. column, "C." should be --- F. ---.

Signed and Sealed this

Twenty-eighth Day of June 1983

[SEAL]

Attest:

GERALD J. MOSSINGHOFF

Attesting Officer

Commissioner of Patents and Trademarks